United States Patent [19]

Schiller

[11] 4,053,228
[45] Oct. 11, 1977

[54] FINGER IDENTIFICATION

[76] Inventor: Michael Schiller, 4465 Douglas Ave., Riverdale, N.Y. 10471

[21] Appl. No.: 640,174

[22] Filed: Dec. 12, 1975

[51] Int. Cl.$^2$ .................. G06K 9/08; G01B 11/24; G06K 9/00
[52] U.S. Cl. .................. 356/71; 340/146.3 E; 356/168
[58] Field of Search .................. 356/71, 162, 168; 340/146.3 E

[56] References Cited

U.S. PATENT DOCUMENTS

| 3,138,059 | 6/1964 | White | 356/156 |
| 3,716,301 | 2/1973 | Caulfield et al. | 356/71 |
| 3,743,421 | 7/1973 | Maloney | 356/71 |

Primary Examiner—John K. Corbin
Assistant Examiner—Stewart Levy
Attorney, Agent, or Firm—McAulay, Fields, Fisher & Goldstein

[57] ABSTRACT

A fingerpress is formed by pressing a finger against the back surface of a transparent glass plate and holding it in a predetermined position thereon. This fingerpress is interrogated by a light beam directed through the front surface of the glass plate. The interrogating beam is partially reflected at the back surface to provide a signal beam carrying fingerpress information. The signal beam is created by virtue of the optical discontinuity between the glass plate and the fingerpress. There is one discontinuity between the glass plate and the air underlying the valleys of the fingerpress and another discontinuity between the glass plate and the finger oil at the crests of the fingerpress. The two discontinuities cause differing amounts of light to be reflected and the signal beam is thus created. The signal beam is correlated against a hologram of the same fingerpress to provide identification. The hologram is created either from a film image of the fingerpress or from the fingerpress in real time. The finger is held in predetermined registration position both in making the hologram, or film on which the hologram is made, and when being interrogated for identification so that correlation can be properly made. The front surface of the glass plate is coated with an anti-reflectant coating and the back surface is coated with a coating to enhance the difference in reflectivity of the valleys and crests of the fingerpress.

22 Claims, 8 Drawing Figures

Fig. 2.

FINGER IDENTIFICATION

BACKGROUND OF THE INVENTION

There are many known techniques of identifying an individual through the identification of the individual's fingerprint. The use of an ink pad and the direct transfer of ink by the thumb or finger from the ink pad to a recording card is the standard way of making this identification.

However, it has long been recognized that there are many limitations and drawbacks to this standard technique and thus many alternate proposals have been made and alternate techniques developed, some of which are in limited use. However, on balance, none of these alternate techniques provide an adequate solution to the problems of the standard technique and, indeed, the alternate techniques all tend to create other problems.

Incidentally, in connection with the discussion and disclosure herein, the term finger will be used in the generic sense to refer to what is commonly known as a thumb as well as to fingers and, indeed, any prints that may be taken of an individual's toes, foot or hand. However, it is convenient for many purposes to use an individual's thumb as an identifying base.

Although the average person is aware of the messy cumbersome nature of the standard ink transfer technique of taking finger-prints, there are even greater problems with the present techniques from the point of view of either law enforcement officials or those who would use the fingerprint for credit or other identification. Essentially, the quality of the fingerprint obtained tends to be poor. Thus, the necessary resolution required to provide ready classification and unambigious identification is missing.

Fingerprint identification has significant potential application in many fields other than law enforcement but is limited to law enforcement fields in most part because of its messy nature and general unacceptability. The other fields in which identification of the unique features of each individual would be useful include all sorts of security situations, credit card identification situations, industrial access identification situations and even in those situations where a signature is used for comparison with the individual's signature on file as in many banking and commercial transactions.

Accordingly, it is a major purpose of this invention to provide a much more acceptable and thus more widely usuable technique for identifying the individual's unique characteristics that are carried by the pattern of the lines and sworls which constitute an individual's finger surface configuration and which when impressed by standard techniques provide the individual's unique fingerprint.

BRIEF DESCRIPTION OF THE INVENTION

In brief, this invention employs not the fingerprint of a subject as such but rather the actual configuration of the surface of the subject's finger. A finger is pressed against the back surface of a transparent glass plate and held in a predetermined position thereon to provide a fingerpress.

A beam of light is directed at the front surface of the glass plate. The light beam substantially passes through the glass plate and at the back surface is partially reflected. There is a first magnitude of reflection at the optical discontinuity between the back surface of the plate and the air underlying the valleys of the fingerpress. There is a second magnitude of reflection at the optical discontinuity between the back surface of the plate and the crests of the fingerpress. This reflected light therefore provides an image of the fingerpress which can then be optically processed downstream by a comparator, a recording device and/or transmitter. The interrogating light beam has an axis which is at a few degrees to the normal of the glassplate so that the beam carrying the fingerpress image will be reflected at an angle which makes it diverge from the interrogating beam.

The front surface of the glass plate is preferably coated with an anti-reflectant coating to minimize reflection of the beam at the optical discontinuity between the front surface of the plate and the air. The back surface is also preferably coated with an appropriate optical material to enhance the difference in the magnitude of reflection between the two optical discontinuities. In one embodiment, the beam of light is coherent light from a laser. A holographic optical correlator downstream processes the reflected light beam. In that embodiment, a previously made holographic image of the subject's fingerpress, incorporated in a security passcard, is inserted in the correlator and the reflected light is optically compared with the stored holographic image to provide a positive identification of the subject with his passcard.

The positioning of the finger on the glass plate is critical to provide an image which can be compared with a previously made holographic image of the comparably positioned fingerpress. Thus a positioning mechanism is provided at the back surface of the glass plate to permit the subject to readily position his finger at a predetermined transverse location along the back surface of the plate. The positioning mechanism together with the plate provides a three dimensional optical registration mechanism for the fingerpress for unambiguous correlation with the hologram.

BRIEF DESCRIPTION OF THE DRAWINGS

FIG. 6 is an optical schematic illustrating the production of the hologram used in the FIG. 1 device from the film negative produced by the FIG. 5 mechanism.

FIG. 8 is an optical schematic similar to that of FIG. 6 illustrating the production of the hologram, used in the FIG. 1 device, from a fingerpress directly without use of the FIG. 5 camera intermediary.

DESCRIPTION OF THE PREFERRED EMBODIMENTS

Figures 1, 2, 3:
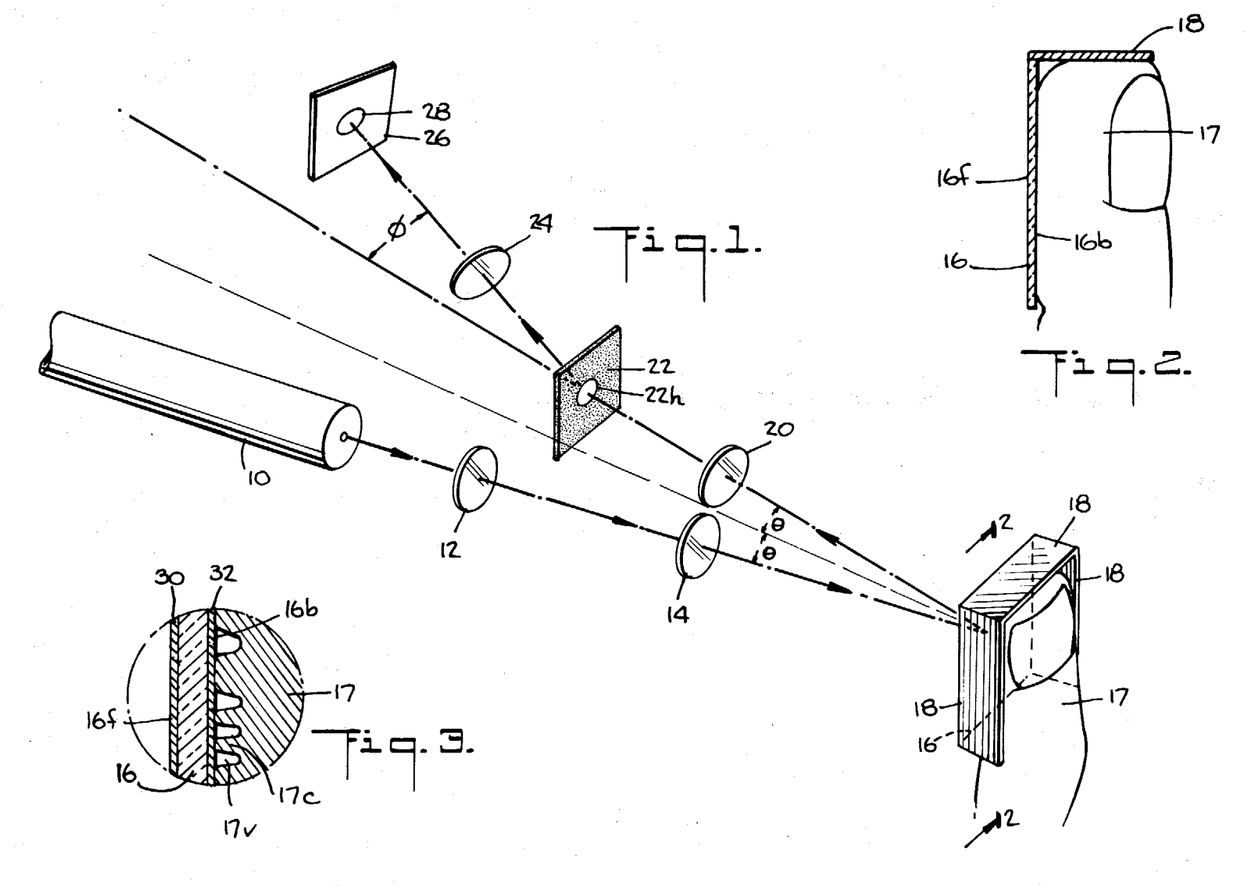
FIG. 1 is an optical schematic of the identification device of this invention.
FIG. 2 is an illustration along the plane 2—2 of FIG. 1 showing a finger in position in the finger rest.
FIG. 3 is an exploded view of a small area under the thumb of FIG. 2 showing the relationship between the glass plate and the finger configuration.

The FIG. 1 Arrangement - Correlation.

FIG. 1 is an optical schematic illustrating the basic elements of an embodiment of this invention. A laser beam source 10 provides a spatially coherent light beam. Two lenses 12 and 14 expand and collimate the light beam to provide an approximately 1.5 inch spatially coherent light beam incident on the front surface 16f of a transparent glass plate 16.

The front surface 16f is coated with a substantially anti-reflectant coating to maximize the portion of the light beam passing through the front surface 16f. The beam will be partially reflected from the back surface 16b of the glass plate 16 because of the optical discontinuity at the back surface. The antireflectant coating on the front surface 16f reduces the non-signal bearing background or pedestal in the reflected modulated beam. The finger 17 to be interrogated or examined is pressed against the back surface 16b of the glass plate 16. Three side panels 18 extend back from the surface 16b of the plate 16 to position the finger that is to be pressed against the plate 16. These panels 18 and the back surface 16b provide a guide and a limit on the position of the finger to be interrogated.

When a finger is pressed against the back surface 16b of the glass plate 16 a surface object is created which is called herein a fingerpress. That portion of the incident light beam which is reflected from the back surface 16b is modulated by the crests and valleys of the fingerpress to provide a reflected light beam that carries identification information.

So that this modulated reflected light beam will not be superimposed on the incident coherent laser beam, the incident beam is directed toward the plate 16 at a small angle theta $\theta$ to the normal. As a consequence the modulated light beam is reflected at the same angle theta to the normal and the two light beam paths diverge from one another by an angle equal to two theta. In order for the anti-reflectant coating to be effective, the angle theta must be kept fairly small. An angle of five degrees (5°) for theta has been found to be both effective and convenient.

The modulated light beam is then processed downstream by a standard optical correlator. The optical correlator consists essentially of a first lens 20, which takes a fourier transform of the modulated light beam, a hologram plate 22 containing a hologram 22h of the predetermined fingerpress, a second lens 24 and an identifying plate 26 containing a single photocell 28.

This holographic optical correlator is of the known off-axis type in that the hologram 22h is generated by the interference pattern between a reference beam and the transform of the reference object wherein the reference beam is at an angle phi $\phi$ to the axis of the beam containing the transform or the reference object. FIG. 6 illustrates the generation of the hologram 22h.

The lens 20 provides the fourier transform of the reflected modulated beam at its back focal plane, where the hologram 22h is positioned. The transform of the beam and the hologram will interact to generate the upper side band correlation beam at an angle phi to the axis of the reflected modulated light beam. In one embodiment, this angle phi is conveniently and usefully made equal to (15°). The unmodulated or d.c. component of the modulated light beam continues through the hologram 22h along the same axis without deviation. However, what is frequently called the upper side band correlation beam proceeds as a light beam along an axis at (15°) to that of the d.c. component.

The second lens 24 completes the optical operation on the upper side band to provide a correlation spot at its back focal plane. The identification plate 26 having the photocell 28 is positioned so that the photocell 28 is at the back focal point of this second lens 24.

As a consequence, if the finger pressed against the back surface 16b of the glass plate 16 is the same as the fingerpress from which the hologram 22h was made, then there will be an auto-correlation which will provide a spot of light at the photocell 28 to generate a photocell 28 output indicating that the individual whose finger is pressed against the plate 16 is the same individual from whom the hologram 22h was made. However, if the wrong finger (either another finger of the same individual or any finger of another individual) is placed against the plate 16, the resulting cross-correlation will provide a sufficiently diffused or spread out image at the plane 26 so that there will not be enough light input to the photocell 28 to cause a photocell output high enough to be read or high enough to go above a predetermined threshold.

Figures 4, 5:
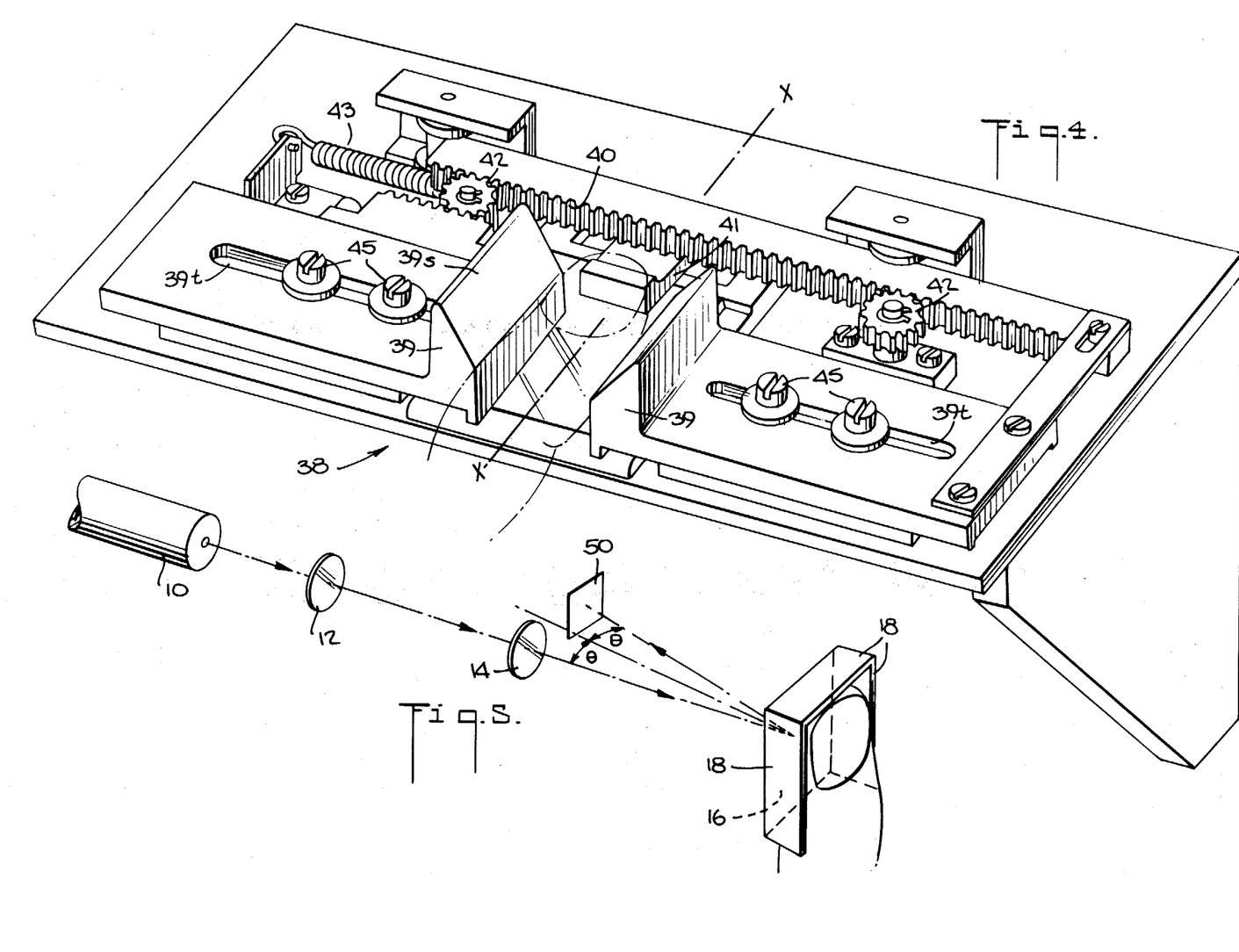
FIG. 4 is a perspective view of a particular finger registration means which has been used in FIG. 1 device for positioning a finger.
FIG. 5 is an optical schematic of an arrangement to provide a film negative of the fingerpress.
Figure 4:
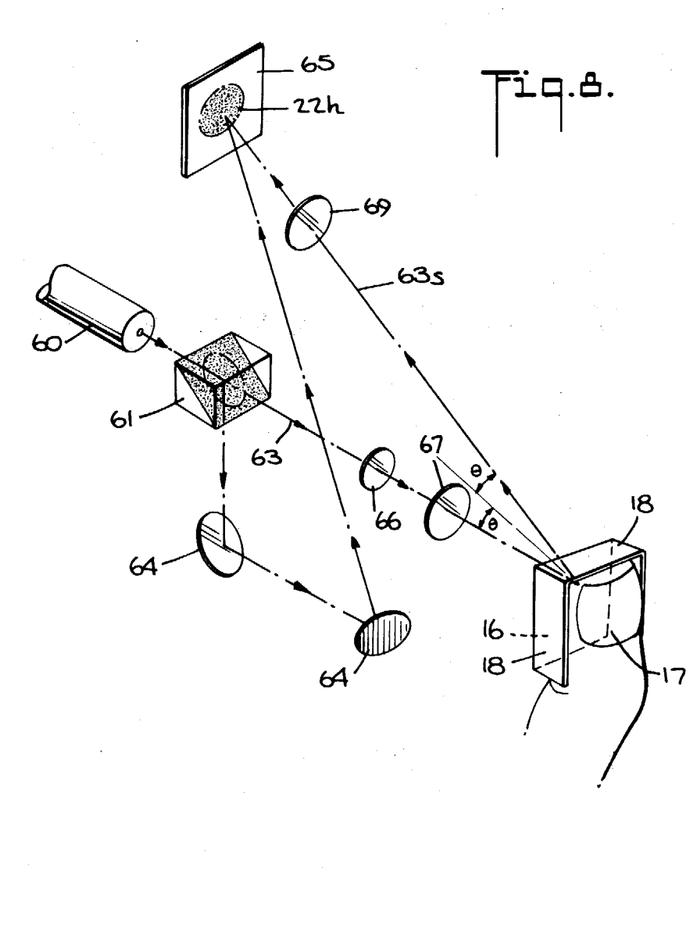
Figure 5:
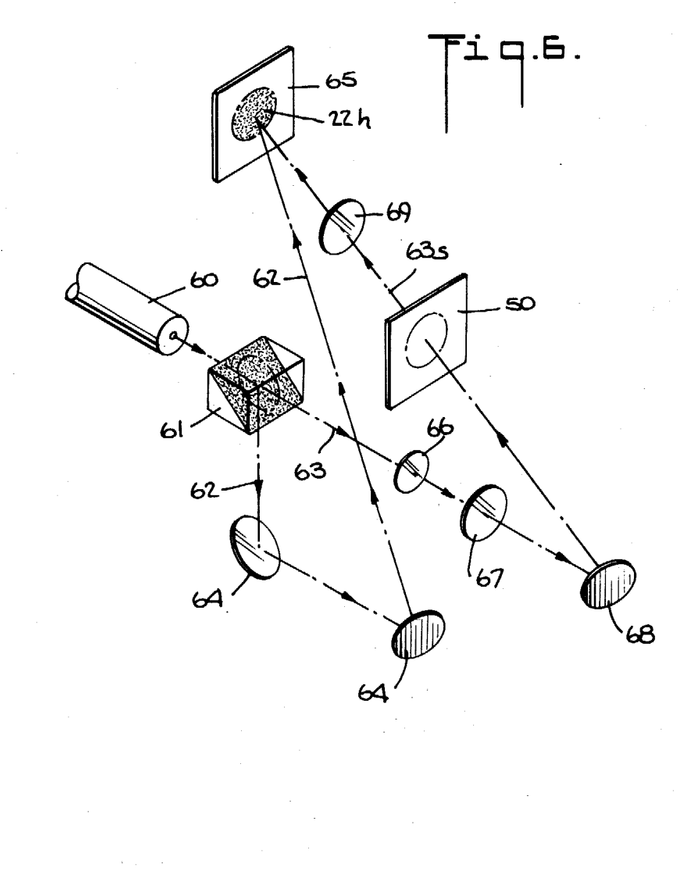

The hologram 22h is generated from a fingerpress and thus is generated from a surface object. In the embodiment disclosed, this fingerpress surface object is a planar surface object. In FIG. 1, a hologram of a planar object, the fingerpress, is matched against a planar image of a fingerpress. When there is a match, the upper side band correlation beam will impinge on the photocell 28. The correlation beam will be displaced if there is displacement of the fingerpress image. Thus it is essential that the fingerpress being interrogated have the same positional relationship to the axis of the interrogating light beam as it had when it was used to form the hologram 22h. The finger positioning structure 18, described in detail in connection with FIG. 4, is used to position the finger for making the hologram 22h and to position the finger for identification against the hologram 22h.

The Fingerpress

The usefulness of the fingerpress may be better appreciated if certain major characteristics of the fingerpress are kept in mind. The fingerpress object as well as the fingerpress image which is projected and processed downstream differ from the finger itself and also differ from the usual ink fingerprint.

The fingerpress is an object characterized by the areas of contact of the crests 17c on the back surface 16b. This creates enhanced visibility for the crest to crest spacing of the finger. That is, at the interface between plate 16 and finger 17 there is created a fingerpress object which is predominantly crests 17c and valleys 17v.

The image of this fingerpress is transmitted downstream as a modulated reflected light beam primarily because of the reflection due to the optical discontinuity between the glass plate 16 and the finger oil. In one embodiment, the match between the index of refraction of the glass plate 16 and the index of refraction of the finger oil minimizes the optical discontinuity and thus minimizes the amount of light reflected at the interface between crests 17c and surface 16b. The mismatch between glass and air at the valleys 17v provides significant reflection because of the optical discontinuity. Thus substantially less light is reflected from the finger crests 17c areas than from the finger valley 17v areas and an image of the fingerpress is thereby transmitted downstream.

In addition, the finger oil fills in pores and other fine irregularities within the crests 17c and thus further reduces the amount of light reflected in the areas of the crests 17c.

In addition, the light which hits the finger crests is absorbed in part by the finger crests thereby aiding in reducing the amount of light reflected at the finger crest areas.

Furthermore, to the extent that there is any light reflected from the finger crests, that light will be in large part scattered by the complex shape of the finger tissue, including pores and fine irregularities in the surface of the crests. The image of the fine irregularities within the crests 17c will diffract appreciably and will not fall within aperture of the hologram 22h, thereby being lost to the identification system.

Thus finger oil fill-in, light absorption by the finger tissues and diffraction all aid the primary effect of the finger oil match in reducing the amount of light, from the interface between finger crests 17c and plate 16, that impinges on the hologram 22h. By contrast, the amount of light reflected at the interface between plate 16 and air (the valleys 17v of the fingerpress) is much greater. In this fashion the effective image projected downstream onto the hologram 22h has a pronounced distinction between finger crest 17c and finger valley 17v.

In a second embodiment, a back surface coating 32 reverses the nature of the interface matching to provide greater reflection at the crests 17c and lesser reflection at the valleys 17v. However, the differential reflection described above still obtains and the fingerpress image is transmitted as a reflected modulated light beam.

The fingerpress arrangement disclosed above provides a correlation between two planes containing information. Specifically, a hologram 22h of a fingerpress is correlated against a reflection from a fingerpress. Both elements being correlated are fingerpress information contained within a plane. FIG. 3 schematically illustrates why this is so. At the surface 16b, between the finger 17 and the plate 16, there are a series of alternating zones. One type of zone is determined by the finger crests 17c and more particularly where the oil from the finger crests is in intimate contact with the surface 16b. The second type of zone is determined by the finger valleys 17v and more particularly where air is in intimate contact with the surface 16b.

The fingerpress thereby created highlights the crest to crest spacing which has a spatial frequency of up to fifteen line pairs per millimeter. The aperture of the hologram 22h is preferably made to cut off at approximately forty line pairs per millimeter. Thus all of the information relating to finger crest 17c spacing is processed and provides a high degree of discrimination between similar fingerpress.

By contrast, a fingerprint, taken with ink, generally has a spatial frequency that only goes up to about five line pairs per millimeter. This is because the ink runs and tends to mask any features finer than five line pairs per millimeter. The fingerpress, accordingly, provides much more information than does the fingerprint and makes possible considerably greater discrimination between similar fingers than can the ink generated fingerprint.

In addition, the fingerpress provides information relating to the shape of the line of demarcation between crests 17c and valleys 17v. This information up to a spatial frequency of about forty line pairs per millimeter, at which the hologram 22h cuts off, is processed by the system and supplements the above mentioned basic crest to crest spacing information. Thereby even greater discrimination is provided.

The fingerpress in conjunction with the system described herein provides substantially more information and thus more discrimination than does a fingerprint. Yet, the fingerpress and system eliminate much of the high frequency components of the finger surface and in particular those spatial frequency components over about forty line pairs per millimeter.

The Plate 16 and Front and Back Plate Surface Coatings.

One transparent plate 16 that has been used in a flat glass plate having an anti-reflectant coating 30 on its front surface 16f and no coating on its back surface 16b. The antireflectant coating is one that is designed to be anti-reflectant to the frequency of the laser beam; 6328 Angstroms (A) in one embodiment. A flat plate 16 has been found to be useful and has been used in an embodiment of this invention. However, the plate 16 could be curved so as to approximately fit the curvature of the typical finger and thus provide a surface adapted to receive the finger to be identified. Accordingly, it should be understood herein that, particularly in the claims, reference to the plate 16 shall include not only the flat plate illustrated but also a curved plate. It is contemplated that a flat plate will be used in the preferred embodiment because when the FIG. 5 camera arrangement is employed, the flat film image of the fingerpress is the object used to make the hologram. In that case, a flat fingerpress is required as the object in the FIG. 1 system in order to have correspondence between object being interrogated and predetermined object.

Unless specified otherwise, it shall be understood in the specification and claims herein, that the reference to the transparent plate 16 means a plate which is substantially transparent to light having the frequency of the laser or other light beam directed thereto.

It shall also be understood herein that, unless otherwise specified, reference to the transparent plate 16 shall include a plate which has various coatings on its surface. For example, it is contemplated that the transparent plate 16 will normally have a standard antireflectant coating 30 on its front surface 16f and it is presently preferred to have such a coating. The antireflectant coating 30 is preferably tuned to the frequency of the laser 10 to provide reflection at the laser frequency as low as 0.15%.

It is also presently preferred to employ a coating 32 on the back surface 16b of the plate 16 in order to enhance the difference in reflection at that surface between those areas where the crests 17c of the finger are in intimate contact with the back surface 16b of the plate and those areas, under the valleys 17v of the finger, where air is in contact with the back surface 16b of the plate. At the finger crests 17c, the discontinuity at the back surface 16b is between the plate 16 and finger oil while at the valleys 17v, the discontinuity is between the plate and air. Where the back surface 16b has a coating 32 to enhance the difference in reflection or reflectivity, the significant discontinuity is between the free surface of the back coating 32 and the finger oil or air. Thus, it should be understood herein that reference to the plate 16 includes reference to a plate having these coatings and reference to the surfaces of the plate includes, where the plate has such coatings, reference to the free surface of the coatings.

There is a small layer of finger oil which establishes the actual intimate contact between the back surface 16b and the crests of the applied fingerpress. It should be understood herein that reference to intimate contact between glass plate and the crests of the finger of reference to the discontinuity between the plate and the crests of the finger includes the normal situation where the actual discontinuity is between the plate and finger oil.

The term "transparent" is used herein in its normal optical sense to refer to a media which does not substantially absorb or block light. However, because of discontinuities in the index of refraction between media, there is the known phenomenon that a certain amount of the light impinging on the discontinuity will be reflected. In that sense, the light is partially reflected and only partially transmitted through the discontinuity. Thus the term "transparent" is understood to mean that the media itself is substantially transparent and, but for the discontinuity, does transmit the light beam. One could use a plate 16 which is less than fully transparent and obtain a degraded but nonetheless substantially similar result. It should be understood herein, particularly in the claims, that reference to a transparent plate shall included any plate which transmit a substantial portion of the light and is not substantially opaque.

On the back surface 16b of the plate 16, a coating is preferably used to enhance the difference in the reflection at the crests of the fingerpress and at the valley of the fingerpress. These coatings are known in the art and can be ordered from various companies by specifying the reflection characteristics desired.

A first back surface 16b coating is specified in the context of a laser beam being applied orthogonal to a glass plate 16 which plate has a front surface 16f that has an anti-reflectant coating thereon. The specification further provides that the coating on the back surface 16b shall be such as to (a) provide a first magnitude of reflection of the laser beam from the back surface 16b when air is in intimate contact with the back surface 16b and (b) to provide a second magnitude of reflection of light when the back surface 16b is in intimate contact with a further layer of glass having the same index of refraction as has the glass plate 16. The specification also provides that the first magnitude of reflection shall be greater than the second magnitude of reflection. Finally, the specification provides that the back surface coating shall be designed to provide as great a difference as possible between the first magnitude of reflection and the second magnitude of reflection.

Finger oil and glass have substantially the same index of refraction. That is why the above specification to the plate manufacturer calls for the second magnitude of reflection on the assumption of a further glass plate as being in intimate contact with the back surface 16b.

What is being specified is a reflection within the context of a layer of glass plate 16, back surface coating and further media (air or additional glass plate). However, it is known in the art to provide products to such a specification. In particular, applicant has obtained, in response to the above specification, a product designated as No. 4437 from Spectra-Physics, Inc. of 1250 West Middlefield Road, Mountain View, California, 94042, and a product designated as No. 7166 from Metavac, Inc. of 44 –68 162 Street, Flushing, New York 11358. The Spectra-Physics product No. 4437 provides a 20% reflection from the back surface 16b when in intimate contact with air and a 7% reflection when in intimate contact with finger oil at the finger crests. The Metavac product No. 7166 provides 15% reflection of laser light where the back surface is in contact with air and less than 1% reflection when in intimate contact with finger oil at the finger crests. In both cases the laser employed has a frequency of 6,328 Angstroms (A).

A second type of back surface 16b coating has also been obtained in which the specification is similar to that set forth above except that it calls for the magnitude of reflection at the discontinuity with a further layer of glass to be greater than the magnitude of reflection at the discontinuity with air. However, this second specification still calls for as great a difference between those two magnitudes of reflection as possible. In connection with this second type of back surface coating, Spectra-Physics provides a product No. 4468 which results in a reflection of approximately 0.5% where the discontinuity is with air 17v and a reflection of 6.8% where the discontinuity is with the oil at the finger crests 17c. A Metavac product No. 7156 provided in response to the specification, results in a reflection of less than 1% where the discontinuity is with air and a reflection of greater than 70% where the discontinuity is at the crests of the fingerpress. The anti-reflectant coating used on the front surface 16f can also be used on the back surface 16b to provide this second type of coating. The anti-reflectant coating is designed to minimize the optical discontinuity between glass and air thus minimizing reflection at that interface. It also greatly enhances reflection at the interface with finger oil.

A wide range of coatings can be provided to obtain the enhanced results; that is, enhanced as contrasted with the situation where no back surface coating 32 is employed. Both of the coatings provided by Spectra-Physics are identified as dielectric hard coatings. Both of the coatings provided by Metavac are transparent conductive hard coatings.

However, it should be recognized that this invention will operate without any coating on the back surface 16b. The use of these coatings enhances the difference in reflection at the discontinuity between the plate and two adjacent media (air and finger oil) so as to provide increased signal power to the holographic correlator.

THE FIG. 4 FINGER POSITIONING DEVICE

FIG. 4 illustrates a specific finger registration mechanism 38 to perform the function shown more schematically as the frame 18 in FIG. 1. The FIG. 4 registration mechanism 38 provides a number of important registration functions. The two side walls 39 are geared through pinions 42 to a common rack 40 so that they both move in unison away from or toward predetermined center line X—X. Thus the finger 17 positioned between the two side walls 39 will always be centrally positioned over a predetermined center line X—X.

The end wall 41 that positions the tip of the finger incorporates a switch and the mechanism involved cannot be enabled unless that switch is closed. This assures that the finger is properly positioned longitudinally along the X axis before the identification check is made. It also prevents a subject from shifting his finger around to try and cheat the machine . In addition, the switch closing assures a subject that he has properly positioned his finger. The end wall 41 is lower than the side walls 39 so that a long fingernail will pass over the end wall 41. It is important that the longitudinal position of the finger be determined by the end of the finger abutting the end wall 41.

The side walls 39 are spring 43 loaded and have sloping surfaces 39s which permit a subject to push the walls 39 apart as he brings his finger down onto the plate 16. The side walls 39 have tracks 39t which ride on pins 45 to maintain side wall 39 alignment.

The glass plate 16 against which the finger 17 rests serves to position the finger along the third dimensional axis, the Z axis. The operation of the side walls 39, plate 16 and end wall 41 in combination also serves to position the finger's rotational orientation in the plane of the glass, the X-Y plane. In particular, the two side walls 39 are made long enough to provide a control over rotational misalignment of the finger in the plane of the glass.

A very important operational routine with the FIG. 4 apparatus is that the individual finger is placed against the end wall 41 switch and once properly positioned along the X axis, the individual rotates or tilts the finger upward to free the ball of the finger from the surface 16b of the plate and then brings the finger back down against the surface 16b. This will eliminate the substantial positional distortion when an individual moves the finger into position across the surface of the glass plate under pressure, thus pushing and squeezing the ball of the finger back out of its normal location. If the finger once positioned is tilted up about the edge of the plate 16 and then brought down, the surface of the finger will be maintained in proper spatial registration. Without this procedural routine, fingerpress repeatability is lost and positive identification may not be made.

This finger positioning structure 38 permits a precise positioning of the correlation spot at the photocell 28. Thus a relatively small aperture at the photocell 28 can be employed and the system discrimination enhanced. System discrimination can be great enough so that it will discriminate between two fingers having otherwise identical patterns if (a) the distance from the tip of the finger to the core of the pattern differs, or (b) if the distance from the center line X—X of the finger to the core of the pattern differs, or (c) if the rotational position of the core differs. Indeed even if the main difference between two fingers is the amount of curvature of the ball, the flattening of the finger in making the fingerpress will result in pattern displacement that can be distinguished by the FIG. 1 device using the FIG. 4 positioning mechanism.

THE FIG. 5 CAMERA ARRANGEMENT

As used herein, the term fingerpress refers to the surface matrix of relatively low spatial frequency crests and valleys, which matrix is generated by pressing a finger against one surface of a substantially transparent plate. This invention is directed to the generation and the use of this fingerpress for identification of an individual.

Since the fingerpress provided is a two dimensional matrix of information and even more importantly, is transmitted as a two dimensional matrix of information, a photograph or other image of the fingerpress can be employed in lieu of the fingerpress when forming the hologram function. Thus it should be understood that a photograph of the fingerpress can be substituted for the fingerpress when generating the hologram. A photograph provides a time lag in the situation; specifically, it permits generating the hologram 22h in other real time. But, whether it is a fingerpress or a photograph of a fingerpress, the entity is distinct from either a fingerprint of the actual finger or the finger configuration itself.

It will normally be more convenient to generate the hologram 22h at a location remote from the individual whose fingerpress is to be represented by the hologram 22h. For this purpose, a film negative of the fingerpress image can be employed. FIG. 5 illustrates the mechanism for generating the film negative of the fingerpress.

The FIG. 5 arrangement is similar to the FIG. 1 arrangement and therefore the same reference numerals are used to indicate like parts. In FIG. 5, the film 50 is positioned as close as possible to the plate 16 as long as the film 50 does not interfere with the interrogating light beam from the lens 14.

The image of the fingerpress will be carried by the reflected modulated light beam. Although this image will diffract as it proceeds downstream, the film 50 can be positioned close enough (within 10 inches of the plate 16) so that the image is useable. The system involves correlation of fingerpress information only up to about 40 line pairs per millimeter. The amount of diffraction of spatial frequencies below 40 line pairs per millimeter is insignificant over ten inches of travel. Any diffraction of substantially higher frequency information would have no effect on the ultimate correlation.

The FIG. 6 Hologram Generating System.

With the film generated by the FIG. 5 apparatus, the system shown in FIG. 6 can be employed to generate the hologram. As shown in FIG. 6, a laser 60 having exactly the same frequency as the laser 10 provides a coherent light beam which is split by a beam splitter 61 to provide a reference beam 62 and an interrogating beam 63.

The reference beam 62 in the FIG. 6 hologram generating system emerges from the laser 60 with the typical 0.5 to 1.0 millimeter diameter. The laser 60 itself provides some collimation but not extensive collimation for the beam and thus the beam 62 expands somewhat as it moves downsteam. The reference beam 62 is steered by mirrors 64 to impinge in the center of a film 65. The laser 60 is positioned an optical distance from the film 65 (on which the hologram 22h is to be generated) by an amount that causes the expanding reference beam 62 to have a diameter of approximately 100 mils (0.1 inches) at the film 65. This, therefore, determines the diameter of the hologram 22h to be generated.

The interrogating beam 63 is collimated and expanded to a desired diameter (1.5 inches in one embodiment) by two lenses 66 and 67 which operate as a beam expander. This beam 63 to be modulated is steered by the mirror 68 through the film negative 50 of the fingerpress image. The modulated beam which emerges from the film negative 50 has its diffraction pattern placed on the film 65 by the lens 69. The lens 69 effects a fourier transform of the diffracting modulated beam and thereby provides a fully diffracted image at the back focal plane of the lens 69. Thus the film 65 must be placed at the back focal plane of the lens 69.

The interaction of the reference beam 62 and the signal beam 63s at the film 65 produces the desired hologram 22h.

If there were no modulating image, the lens 69 would effectively focus all of the light in the signal beam down to a spot on the film 65 under one mil (0.001 inches).

However, the modulation components diffract so as to provide a much wider diameter diffraction image that is focused by the lens 69 onto its back focal plane where the film 65 is positioned. The lower spatial frequency components diffract less and the higher spatial frequency components diffract more. Because the reference beam 62 is limited to 0.1 inches at the film 65, the hologram generated is a hologram solely of those spatial frequency components which diffract less than 0.1 inches. In effect, this means that the hologram 22h represents those components of the fingerpress image which have a spatial frequency up to approximately 40 line pairs per millimeter.

It is this hologram which is used in the FIG. 1 correlation system. Therefore, in the FIG. 1 correlation system, the only elements of the fingerpress which are effective to affect whether or not correlation is found are those relatively low spatial frequency components; specifically those having a spatial frequency of up to approximately 40 line pairs per millimeter.

The hologram 22h can be generated by using the actual fingerpress rather than a film image of the fingerpress. In such case, the interrogating beam 63 will reflect off the properly positioned fingerpress in the fashion shown and described in connection with FIG. 1. It is contemplated, however, that the use of a film image will generally be more convenient.

As indicated above, the plate 16 can, in general, be curved to approximate the curvature of an average finger. The reason a curved surface fingerpress can be used instead of a flat surface fingerpress is essentially because of the low spatial frequency nature of the fingerpress. However, where a film image of the fingerpress is used to make the hologram 22h, then the glass plate 16 must be flat in both the FIG. 5 camera and the FIG. 1 correlator.

FIG. 8 illustrates the real time technique for generating the hologram. The same reference numbers are used in FIG. 8 as in FIGS. 6 and 1 to indicate the same structure and function. Thus in FIG. 8, the signal beam 63s is formed, as in FIG. 1, by reflection off the back surface 16b of the glass plate. As in FIG. 6, the interference between the signal beam 63s and the reference beam 62 at the back focal plane of the lens 69 forms the hologram 22h.

Figure 7:
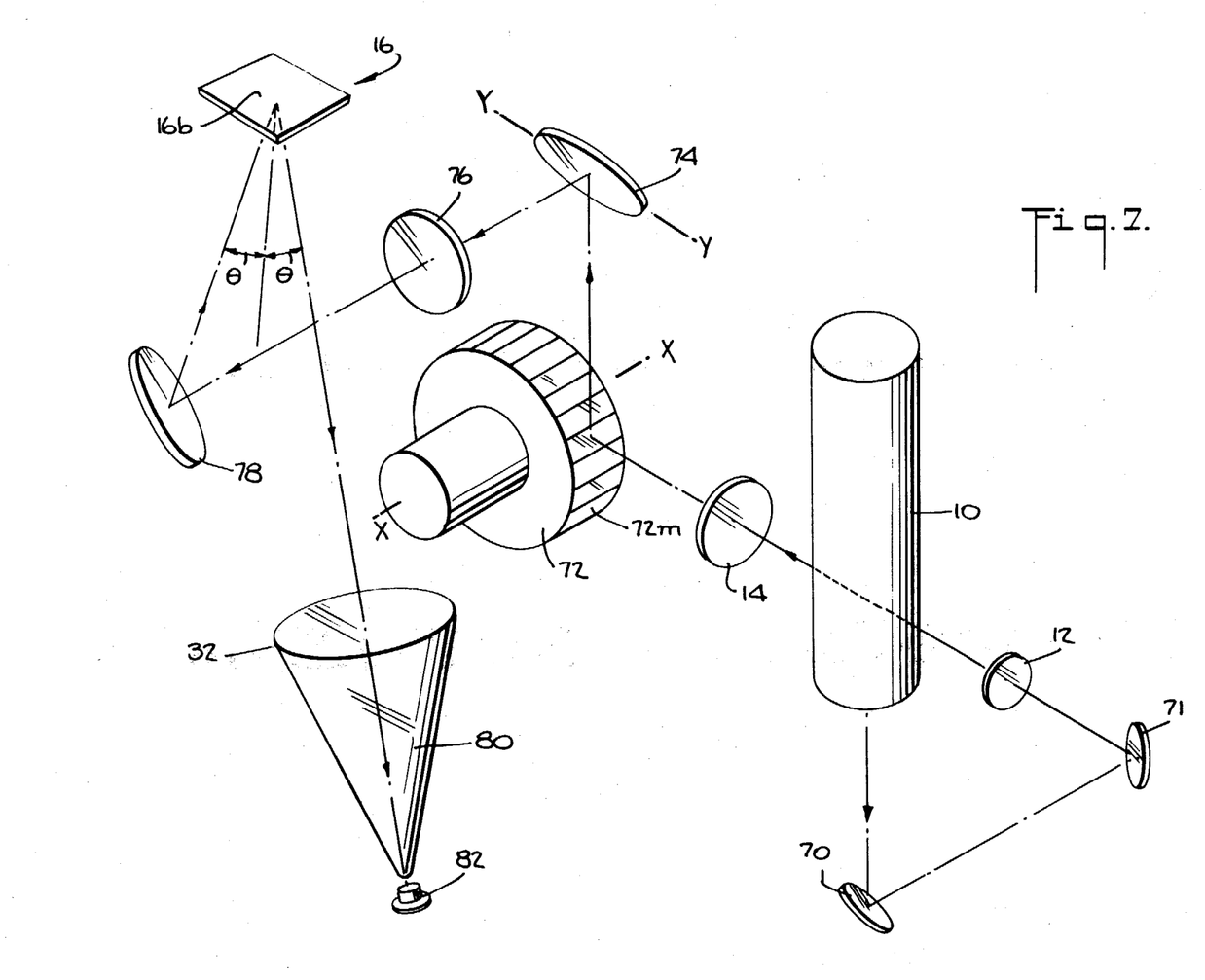
FIG. 7 is an optical schematic of a scanning technique that may be employed in lieu of the FIG. 1 arrangement to provide the fingerpress information in serial form for transmission to a remote location, at which remote location comparison with the hologram of the fingerpress may be made to determine identity.

The FIG. 7 Scanning Apparatus

There are circumstances in which the correlation described in connection with the FIG. 1 system is not to be or cannot be performed where the individual being identified is located. The corresponding hologram may be at a remote location. In such circumstances, a scan of the fingerpress at the plate 16 will provide serial information which can be transmitted over a communications link such as a telephone line to a remote location where the image can be regenerated for correlation against an appropriate hologram 22h at the remote location.

The FIG. 7 arrangement illustrates one feasible scanning mechanism that can be employed to provide this result. As shown in FIG. 7 the laser 10 provides a light beam which is steered by two mirrors 70 and 71 through the collimating lenses 12 and 14. Where the parts in the FIG. 7 arrangement are similar to the parts in the FIG. 1 system, the same reference numerals will be used. The collimated light beam emerging from the lens 14 is caused to sweep along an X axis by a rotating drum 72 of mirrors 72m. A mirror 74 rotating along the axis shown provides the Y axis sweep of the light beam.

The legs 76 serves to focus the light beam emerging from the mirror 74 onto a "point" having a diameter of approximately 1.5 mils (0.0015 inches) at the glass plate 16. For purpose of ease of illustration in FIG. 7, the finger 17 and frame 18 are not shown at the plate 16 but it should be understood that the arrangement shown in FIGS. 1 and 2 obtains at the plate 16 in FIG. 7. A further mirror 78 is positioned to cause the light beam focused on the plate 16 to have an angle theta (preferably 5°) with the normal to the plate so that the scanning light beam can be reflected from the plate along a useable axis free from interference with the other elements of the system. The modulated scanning light beam is collected by a light collection arrangement 80 to focus the beam onto a photo-receptor 82. Various light collector systems are known and a shaped fiber optic bundle could be employed. However, a solid lucite cone, as shown, which is silvered on the outside has been found to be an inexpensive and effective light collector 80 in the system of this invention.

In connection with the FIG. 7 scanning mechanism it must be recognized that there is no necessity to distinguish gray scales but only to identify each scanned segment or cell of the plate 16 as being either black or white. It is this two level discrimination which permits the relatively simple arrangement shown in FIG. 7. When the image being scanned is below a certain light threshold, then the photo-receptor 82 provides no output. When the element being scanned is above that threshold, then the photo-receptor 82 and associated circuitry provides a full value output for transmission over a telephone line. A timing and synchronizing mechanism (not shown) of a standard type of design can be employed to quantize the scan and identify each element of the scan pattern. A synchronizing mechanism is required to make sure that the serial information starts with the start of the scanning pattern on a raster.

The lens 76 preferably has a long focal length, 400 millimeters being employed in one embodiment, to reduce the criticality of the plate 16 position.

In one embodiment, it is contemplated that a drum 72 having 20 facets 72m, each spaced from the drum axis by 2.475 inches will be effective to provide an X-axis sweep once for each 18° of drum rotation. The drum will be rotating at 1,800 revolutions per minute. The mirror 74 rotates through an arc of approximately 10° once for each X-axis scan. The drive (not shown) for the mirror 74 is cammed to provide a linear sweep for the operative 10° rotation for the mirror 74 with a fast fly back at the end of each 10° scan. The mirror 74 will go through 18 cycles each minute where the 20 facet drum rotates at 1,800 r.p.m.

I claim:
1. Identification apparatus comprising:
   a source of spatially coherent light to provide an interrogating beam,
   a plate transparent to said interrogating beam, said plate having first and second surfaces, said second surface being adapted to receive a fingerpress,
   said beam being directed to said first surface of said plate,
   said beam being partially reflected at said second surface of said plate when a fingerpress is applied at said second surface to provide a reflected light beam modulated with identification information, said partial reflection having a first magnitude at an optical discontinuity between said plate and the finger crests applied thereto, said partial reflection having a second magnitude substantially different from said first magnitude at an optical discontinuity between said plate and air, said beam being substantially orthogonal to the plane of said first and second surfaces to provide said reflected light beam with spatially undistorted identification information and optimized signal to d.c. ratio, said reflected light beam containing spatial frequencies down to zero to provide finger geometry information and indentification means optically coupled to said reflected light beam.

2. The identification apparatus of claim 1 further comprising:
a first coating on said first surface of said plate, said first coating being substantially anti-reflectant to said beam.

3. The identification apparatus of claim 1 further comprising:
a permanent second coating on said second surface of said plate to enhance said difference between said first and said second magnitudes of partial reflection.

4. The fingerpress identification apparatus of claim 1 further comprising:
positioning means at said second surface of said transparent plate for positioning the fingerpress at a predetermined location on said second surface of said plate, said plate and said positioning means providing a constraint on three linear degrees of freedom and one rotational degree of freedom for the fingerpress, said rotational degree of freedom being the one about the optical axis of the apparatus.

5. The identification apparatus of claim 4 further comprising:
a first coating on said first surface of said plate, said first coating being substantially anti-reflectant to said beam.

6. The identification apparatus of claim 5 further comprising:
a second coating on said second surface of said plate to enhance said difference between said first and said second magnitudes of partial reflection.

7. The identification apparatus of claim 4 wherein said identification means comprises:
an off-axis holographic correlator coupled to the light reflected from said second surface of said plate,
said correlator including a hologram of a predetermined fingerpress.

8. The identification apparatus of claim 7 further comprising:
a first coating on said first surface of said plate, said first coating being substantially anti-reflectant to said beam.

9. The identification apparatus of claim 8 further comprising:
a second coating on said second surface of said plate to enhance said difference between said first and said second magnitudes of partial reflection.

10. The identification apparatus of claim 7 further comprising:
a second coating on said second surface of said plate to enhance said difference between said first and said second magnitudes of partial reflection.

11. The identification apparatus of claim 4 wherein said identification means comprises:
an image recording means optically coupled to the light reflected from said second surface of said plate.

12. The identification apparatus of claim 11 further comprising:
a first coating on said first surface of said plate, said first coating being substantially anti-reflectant to said beam.

13. The identification apparatus of claim 12 further comprising:
a second coating on said second surface of said plate to enhance said difference between said first and said second magnitudes of partial reflection.

14. The identification apparatus of claim 4 further comprising:
scanning means to cause said interrogating beam to scan whatever fingerpress is at said second surface of said plate, and
wherein said identification means comprises optical collection means to collect said reflected beam and provide a serial signal representing the optical discontinuities at said back surface of said plate.

15. The identification apparatus of claim 14 further comprising:
a first coating on said first surface of said plate, said first coating being substantially anti-reflectant to said beam.

16. The identification apparatus of claim 15 further comprising:
a second coating on said second surface of said plate to enhance said difference between said first and said second magnitudes of partial reflection.

17. The method of providing a fingerpress of an individual for identification purposes comprising the steps of:
applying the finger of the individual to be identified against a back surface of a transparent plate,
holding said finger laterally centered over a longitudinal axis,
moving said finger longitudinally against a stop to provide a longitudinal position for said finger,
tilting said finger up and rotating said finger back down against said back surface to properly position the core of said fingerpress,
projecting an interrogating coherent light beam toward the front surface of said plate, said interrogating light beam being substantially orthogonal, yet being off axis to said plate,
reflecting a first portion of the light incident on the optical discontinuity between said plate and the finger ridges applied thereto, and
reflecting a second portion of the light incident on the optical discontinuity between said plate and the air underlying the finger valleys, the magnitude of said second portion being substantially different from the magnitude of said first portion.

18. The method of identifying an individual comprising the steps of:
positioning a fingerpress of the individual at a first predetermined position on a second surface of a transparent plate having first and second surfaces,
projecting an interrogating beam of spatially coherent light toward said first surface of said plate, said interrogating light beam being substantially orthogonal to said first and second surfaces, reflecting a portion of said interrogating beam at the optical discontinuity at said second surface of said plate to provide a reflected light beam modulated with identification information.

said step of reflecting including the step of spatially modulating said reflected light beam by reflecting a first portion of the light incident at the discontinuity between said plate and the crests of the fingerpress applied thereto and a second portion at the discontinuity between said plate and the air valleys of the fingerpress applied thereto, said second portion being substantially different in magnitude than said first portion, said step of modulating including providing a reflected light beam with spatially undistorted identification information, an optimized signal to d.c. ratio and finger geometry information contained in spatial frequencies down to zero and processing said reflected light beam to provide identification of said finger press.

19. The method of claim 18 wherein said step of processing comprises:

generating a hologram of a predetermined fingerpress, and holographically correlating the reflected light against said hologram.

20. The method of claim 19 further comprising the step of:

positioning said predetermined fingerpress at a second predetermined position on a transparent plate to provide said fingerpress for said step of generating a hologram, said second predetermined position having a predetermined relationship to said first predetermined position.

21. The method of claim 20 wherein:

said step of positioning comprises positioning the fingerpress at a flat transparent plate, and said step of generating a hologram comprises the steps of photographing a predetermined planar fingerpress, and generating a hologram of the image of said planar fingerpress from said photograph.

22. The method of claim 20 wherein said hologram is generated directly from said predetermined fingerpress in real time.

* * * * *